(12) United States Patent
Gulachenski et al.

(10) Patent No.: US 9,884,172 B2
(45) Date of Patent: Feb. 6, 2018

(54) REINFORCED BALLOON CATHETER

(75) Inventors: Joseph Gulachenski, Trabuco Canyon, CA (US); Cathy Lei, Chino Hills, CA (US); Nelson Peralta, Rancho Santa Margarita, CA (US); Tadele Haile, Cypress, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 308 days.

(21) Appl. No.: 13/405,113

(22) Filed: Feb. 24, 2012

(65) Prior Publication Data

US 2012/0245521 A1 Sep. 27, 2012

Related U.S. Application Data

(60) Provisional application No. 61/446,879, filed on Feb. 25, 2011.

(51) Int. Cl.
*A61M 25/10* (2013.01)
*A61M 25/00* (2006.01)

(52) U.S. Cl.
CPC ...... *A61M 25/1036* (2013.01); *A61M 25/005* (2013.01); *A61M 25/0045* (2013.01); *A61M 25/0053* (2013.01); *A61M 25/10* (2013.01); *A61M 25/1006* (2013.01); *A61M 25/1034* (2013.01); *A61M 25/0012* (2013.01); *A61M 2025/1061* (2013.01);
(Continued)

(58) Field of Classification Search
CPC ............... A61M 25/10; A61M 25/005; A61M 25/1011; A61M 25/0053; A61M 2025/0063; A61M 25/0012; A61M 25/008; A61M 2025/0004; A61M 25/003; A61M 25/1006; A61M 2025/0018; A61M 2025/1065; A61M 2025/1013; A61M 2025/1081; A61M 2025/1061; A61M 2025/1077; A61M 2025/1079; A61M 2025/1093; A61M 25/0045; A61M 25/1034; A61M 25/1036; A61M 2025/1084; A61M 2025/1056
USPC ....................................... 604/103.09
See application file for complete search history.

(56) References Cited

U.S. PATENT DOCUMENTS 3,045,677 A 5/1960 Wallace
3,225,762 A 12/1965 Guttman
(Continued)

FOREIGN PATENT DOCUMENTS

CN 103648575 A 3/2014
EP 2376171 10/2001
(Continued)

OTHER PUBLICATIONS

Japan Patent Office, Notice of Allowance dated Apr. 30, 2014 in Japanese Patent Application No. 2011-540902, 3 pages.
(Continued)

*Primary Examiner* — Nathan R Price
*Assistant Examiner* — Weng Lee
(74) *Attorney, Agent, or Firm* — Inskeep IP Group, Inc.

(57) ABSTRACT

One embodiment of the present invention discloses a balloon catheter employing a reinforced, co-axial, duel lumen design. In certain embodiments, at least one of the lumens is formed of a multilayer, tubular element in which one of the layers functions, in part, to provide radial reinforcement to the tubular element.

24 Claims, 7 Drawing Sheets

(52) U.S. Cl.
CPC ........... *A61M 2025/1077* (2013.01); *A61M 2025/1079* (2013.01); *A61M 2025/1093* (2013.01); *Y10T 29/49826* (2015.01)

(56) References Cited

U.S. PATENT DOCUMENTS

| | | | |
|---|---|---|---|
| 3,537,451 A | | 11/1970 | Murray |
| 3,559,643 A | | 2/1971 | Pannier, Jr. et al. |
| 3,570,485 A | | 3/1971 | Reilly |
| 3,742,958 A | | 7/1973 | Rundles |
| 3,769,975 A | | 11/1973 | Nimoy et al. |
| 3,815,608 A | | 6/1974 | Spinosa et al. |
| 3,853,130 A | | 12/1974 | Sheridan |
| 3,877,429 A | | 4/1975 | Rasumoff |
| 4,306,562 A | | 12/1981 | Osborne |
| 4,323,071 A | * | 4/1982 | Simpson ........... A61M 25/0054 128/DIG. 18 |
| 4,402,685 A | | 9/1983 | Buhler et al. |
| 4,412,832 A | | 11/1983 | Kling et al. |
| 4,449,973 A | | 5/1984 | Luther |
| 4,638,805 A | * | 1/1987 | Powell ................. A61M 25/10 604/913 |
| 4,663,358 A | | 5/1987 | Hyon et al. |
| 4,709,698 A | | 12/1987 | Fogarty |
| 4,739,768 A | | 4/1988 | Engelson |
| 4,808,155 A | | 2/1989 | Mahurkar |
| 4,840,613 A | | 6/1989 | Balbierz |
| 4,884,579 A | | 12/1989 | Engelson |
| 4,887,997 A | | 12/1989 | Okada |
| 4,932,946 A | | 6/1990 | Shields |
| 4,988,356 A | | 1/1991 | Crittenden et al. |
| 4,994,032 A | * | 2/1991 | Sugiyama et al. ....... 604/103.09 |
| 5,011,488 A | | 4/1991 | Ginsburg |
| 5,135,486 A | * | 8/1992 | Eberle ................. A61M 25/104 604/103.1 |
| 5,135,487 A | * | 8/1992 | Morrill et al. ........... 604/103.09 |
| 5,234,411 A | | 8/1993 | Vaillancourt |
| 5,250,033 A | | 10/1993 | Evans et al. |
| 5,258,042 A | | 11/1993 | Mehta |
| 5,279,590 A | | 1/1994 | Sinko et al. |
| 5,279,596 A | * | 1/1994 | Castaneda et al. .......... 604/525 |
| 5,413,791 A | | 5/1995 | Rhee et al. |
| 5,489,273 A | | 2/1996 | Whitney et al. |
| 5,509,910 A | | 4/1996 | Lunn |
| 5,549,557 A | | 8/1996 | Steinke et al. |
| 5,570,585 A | | 11/1996 | Vaynberg |
| 5,662,622 A | | 9/1997 | Gore et al. |
| 5,693,085 A | | 12/1997 | Buirge et al. |
| 5,702,373 A | | 12/1997 | Samson |
| 5,711,909 A | | 1/1998 | Gore et al. |
| 5,728,063 A | * | 3/1998 | Preissman et al. ...... 604/103.09 |
| 5,728,065 A | * | 3/1998 | Follmer ................. A61M 25/10 604/96.01 |
| 5,733,400 A | | 3/1998 | Gore et al. |
| 5,772,641 A | | 6/1998 | Wilson |
| 5,895,378 A | | 4/1999 | Berenstein et al. |
| 5,906,605 A | | 5/1999 | Coxum |
| 5,906,606 A | * | 5/1999 | Chee ................. A61M 25/005 604/246 |
| 5,928,260 A | | 7/1999 | Chin et al. |
| 6,015,424 A | | 1/2000 | Rosenbluth et al. |
| 6,042,578 A | | 3/2000 | Dinh et al. |
| 6,152,912 A | | 11/2000 | Jansen et al. |
| 6,159,197 A | | 12/2000 | Heuser |
| 6,165,193 A | | 12/2000 | Greene, Jr. et al. |
| 6,186,978 B1 | | 2/2001 | Samson et al. |
| 6,193,691 B1 | | 2/2001 | Beardsley |
| 6,210,396 B1 | | 4/2001 | MacDonald et al. |
| 6,296,631 B2 | | 10/2001 | Chow |
| 6,299,619 B1 | | 10/2001 | Greene, Jr. et al. |
| 6,361,528 B1 | | 3/2002 | Wilson et al. |
| 6,447,540 B1 | | 9/2002 | Fontaine et al. |
| 6,451,005 B1 | | 9/2002 | Saitou et al. |
| 6,500,190 B2 | | 12/2002 | Greene, Jr. et al. |
| 6,503,353 B1 | | 1/2003 | Peterson et al. |
| 6,524,274 B1 | | 2/2003 | Rosenthal et al. |
| 6,623,450 B1 | | 9/2003 | Dutta |
| 6,629,952 B1 | * | 10/2003 | Chien ................. A61M 25/005 604/103.09 |
| 6,656,214 B1 | | 12/2003 | Fogarty et al. |
| 6,723,108 B1 | | 4/2004 | Jones et al. |
| 7,066,904 B2 | | 6/2006 | Rosenthal et al. |
| 7,229,454 B2 | | 6/2007 | Tran et al. |
| 7,695,488 B2 | | 4/2010 | Berenstein et al. |
| 7,749,234 B2 | * | 7/2010 | Euteneuer et al. ........... 606/108 |
| 2002/0156459 A1 | | 10/2002 | Ye et al. |
| 2003/0055374 A1 | | 3/2003 | Martins et al. |
| 2003/0195490 A1 | | 10/2003 | Boatman et al. |
| 2004/0103516 A1 | | 6/2004 | Bolduc |
| 2004/0138625 A1 | | 7/2004 | Flodin |
| 2004/0243102 A1 | | 12/2004 | Berg et al. |
| 2005/0183729 A1 | | 8/2005 | Fischer |
| 2005/0245897 A1 | | 11/2005 | Bolduc et al. |
| 2006/0106421 A1 | | 5/2006 | Teoh |
| 2006/0116636 A1 | | 6/2006 | Murphy et al. |
| 2006/0155302 A1 | | 7/2006 | Sisken et al. |
| 2006/0229553 A1 | | 10/2006 | Hammack |
| 2006/0264905 A1 | | 11/2006 | Eskridge et al. |
| 2007/0005092 A1 | * | 1/2007 | Godin ............... A61M 25/0023 606/194 |
| 2007/0135734 A1 | | 6/2007 | Reynolds et al. |
| 2007/0250101 A1 | | 10/2007 | Horn et al. |
| 2008/0167628 A1 | | 7/2008 | Li et al. |
| 2008/0228171 A1 | | 9/2008 | Kugler |
| 2010/0057018 A1 | | 3/2010 | Lentz et al. |

FOREIGN PATENT DOCUMENTS

| | | |
|---|---|---|
| JP | 62186701 | 11/1987 |
| JP | 2001-190681 A | 7/2001 |
| JP | 2007330628 | 12/2007 |
| WO | WO9737714 A1 | 10/1997 |
| WO | WO1997/048326 A2 | 12/1997 |
| WO | WO2000/069502 A1 | 11/2000 |
| WO | WO2004/033015 A1 | 4/2004 |
| WO | WO10059519 A1 | 5/2010 |
| WO | WO2010/068793 A1 | 6/2010 |

OTHER PUBLICATIONS

United States Paten and Trademark Office, Final Office Action dated Feb. 4, 2014, in U.S. Appl. No. 13/405,113, 13 pages.
European Patent Office, Supplementary European Search Report dated Oct. 23, 2013 in European Patent Application No. 12749846.7, 10 pages.
European Patent Office, Supplementary European Search Report dated Oct. 23, 2013 in European Patent Application 12749846.7, 10 pages.
European Patent Office, Examination Report dated Oct. 17, 2013 in European Patent Application No. 09832559.0, 4 pages.
State Intellectual Property Office, P.R. China, Second Office Action dated Sep. 10, 2013 with English translation in Chinese Patent Application No. 200980149936.8, 12 pages.
Japan Patent Office, Official Action dated Sep. 20, 2013 in Japanese Patent Application Serial No. 2011-540902 (English translation), 2 pages.
United States Patent and Trademark Office, Office Action dated Jun. 10, 2013, in U.S. Appl. No. 13/405,113, 10 pages.
State Intellectual Property Office, P.R. China, First Office Action dated Dec. 24, 2012 with English translation in Chinese Patent Application No. 200980149936.8, 11 pages.
United States Patent and Trademark Office, Final Office Action dated Dec. 6, 2012 in U.S. Appl. No. 12/635,465, 13 pages.
United States Patent and Trademark Office, Office Action dated Sep. 5, 2013 in U.S. Appl. No. 12/188,581, 14 pages.
WIPO, U.S. International Search Authority, International Search Report and Written Opinion dated Jun. 28, 2012 in International Patent Application 13/405,113, 8 pages.
United States Patent and Trademark Office, Office Action dated Jun. 12, 2012 in U.S. Appl. No. 12/635,465, 9 pages.

(56) References Cited

OTHER PUBLICATIONS

European Patent Office, Supplementary European Search Report dated Apr. 19, 2012 in European Patent Application No. 09832559.0, 7 pages.
United States Patent and Trademark Office, Final Office Action dated Jan. 20, 2011 in U.S. Appl. No. 12/188,581, 17 pages.
United States Patent and Trademark Office, Office Action dated Jun. 28, 2010 in U.S. Appl. No. 12/188,581, 13 pages.
WIPO, U.S. International Searching Authority, International Search Report dated Feb. 3, 2010 in International Patent Application No. PCT/US2009/067554, 8 pages.
United States Patent and Trademark Office, Office Action dated Oct. 2, 2009 in U.S. Appl. No. 12/188,581, 15 pages.
United States Patent and Trademark Office, Final Office Action dated Jul. 11, 2007 in U.S. Appl. No. 10/755,249, 17 pages.
United States Paten and Trademark Office, Office Action dated Dec. 1, 2006 in U.S. Appl. No. 10/755,249, 30 pages.
Japan Patent Office, English Translation of Official Action dated Sep. 14, 2015 in Japanese Patent Application Serial No. JP2013-555624, 9 pages.
Japan Patent Office, English Translation of Final Official Action dated May 10, 2016 in Japanese Patent Application Serial No. JP2013-555624, 6 pages.
Australia Patent Office, Second Examination Report dated Jan. 20, 2016 in Australian Patent Application Serial No. 201222114, 3 pages.

* cited by examiner

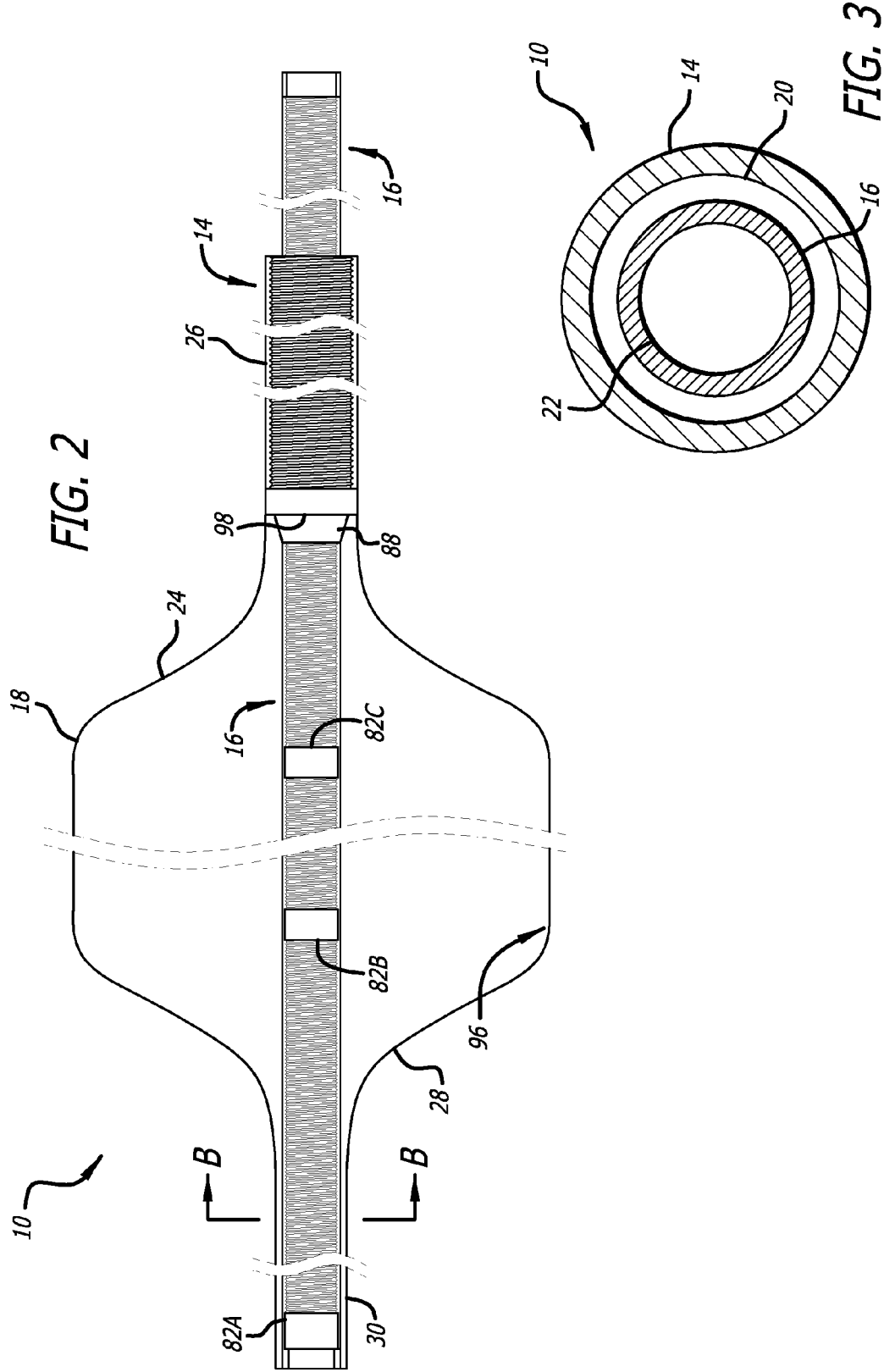

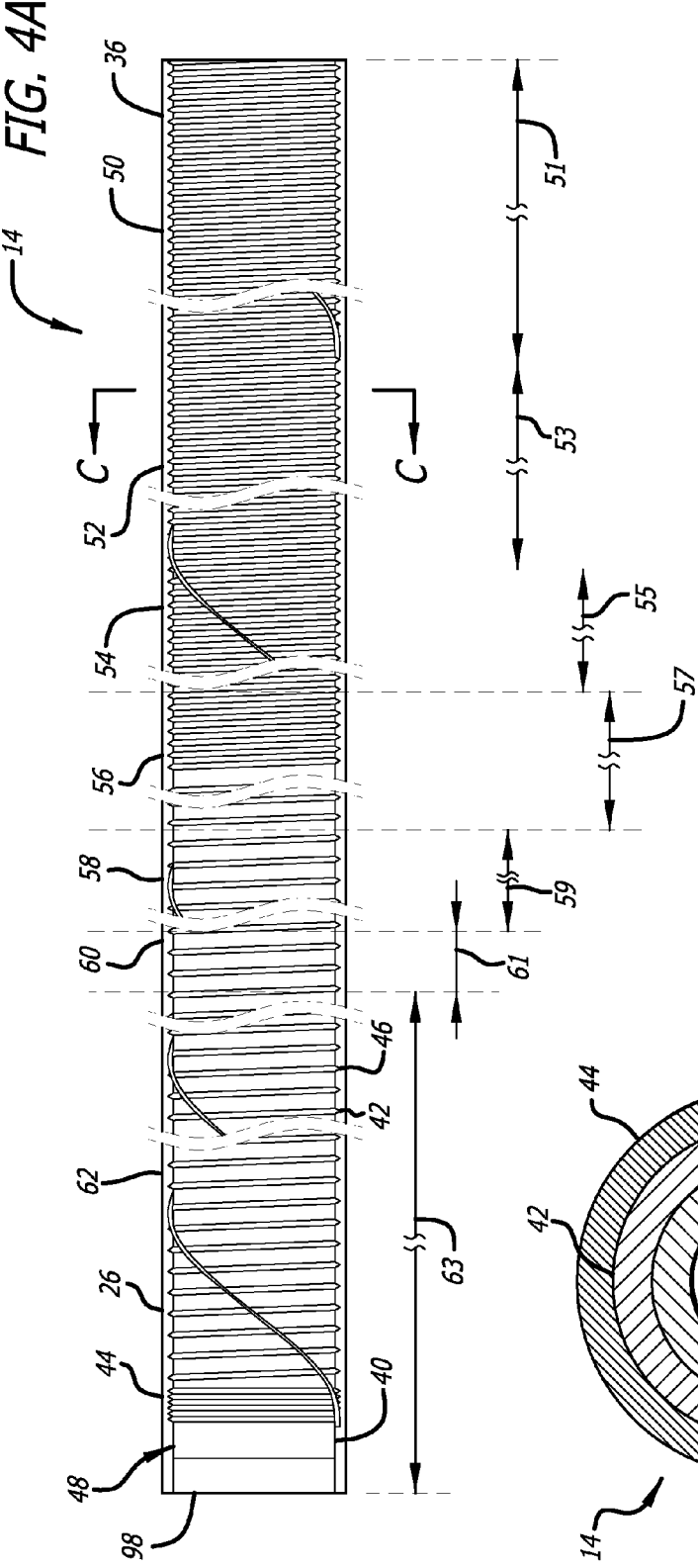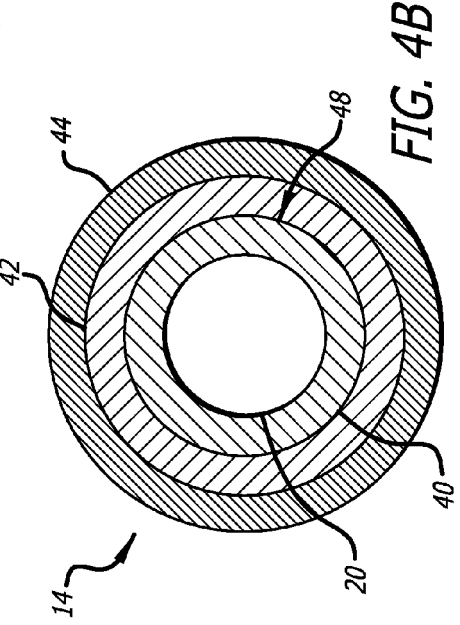

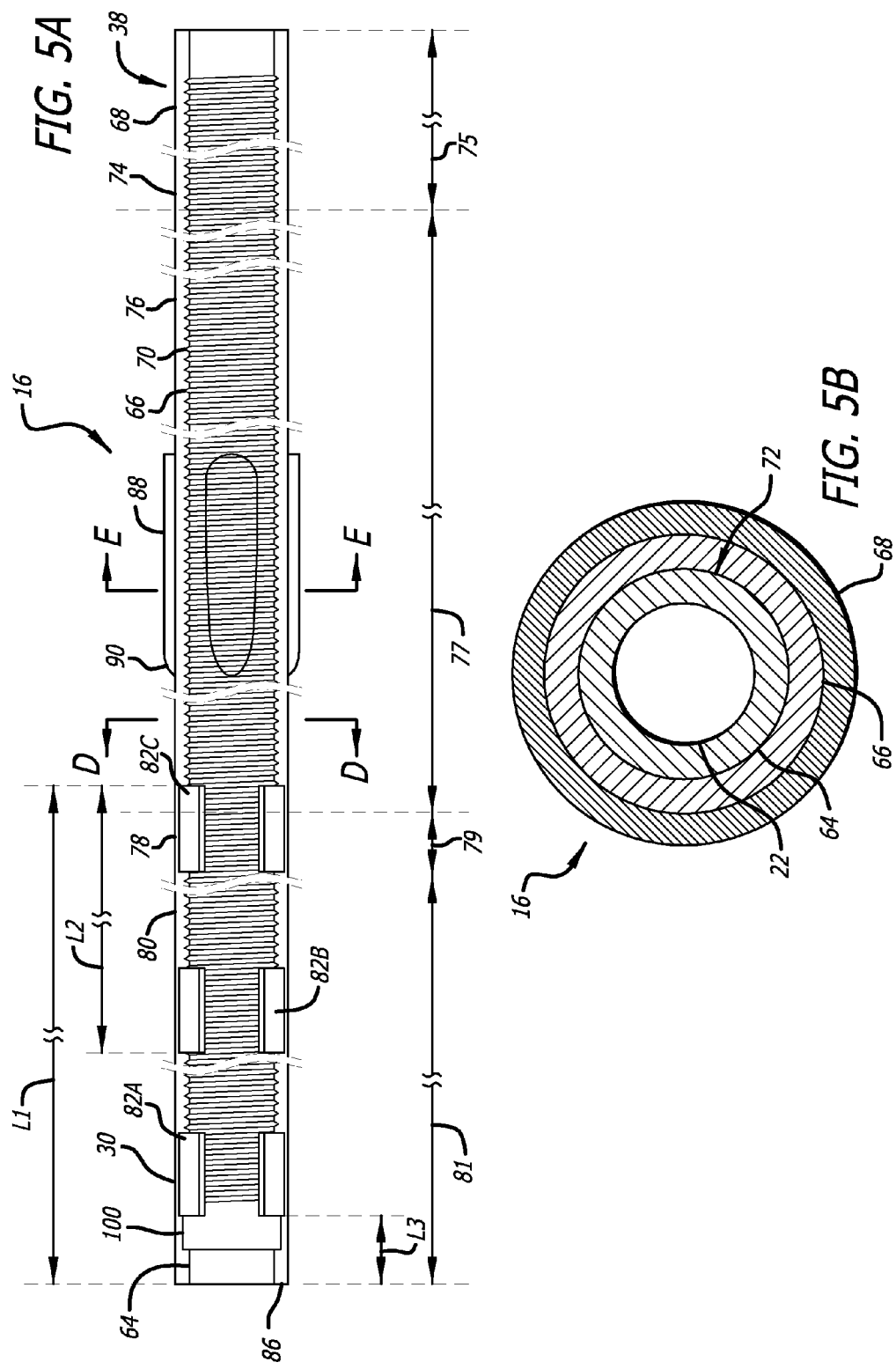

REINFORCED BALLOON CATHETER

RELATED APPLICATIONS

This application claims priority to U.S. Provisional Application Ser. No. 61/446,879 filed Feb. 25, 2011, entitled Reinforced Balloon Catheter, which is hereby incorporated by reference in its entirety.

FIELD OF THE INVENTION

The present invention relates to balloon catheters and, more particularly, to balloon catheters having a plurality of reinforced, co-axially oriented lumens.

BACKGROUND OF THE INVENTION

Balloon catheters are increasingly being employed to conduct neurological procedures in patients. However, the design parameters for balloon catheters intended for use in neurological procedures are significantly different than the design parameters for balloon catheters used in non-neurological procedures such as cardiological procedures. For example, the width of the circulatory system within the neuroanatomy is significantly smaller and more tortuous than the circulatory system in other parts of the body. In order to access the smaller and more tortuous regions of the neuroanatomy, it is necessary to minimize the outer diameter of the balloon catheter while simultaneously maintaining the pushability and trackability of the catheter.

In order to minimize the outer diameter, current balloon catheters intended for neurological procedures employ a non-reinforced, single lumen, over-the-wire design. Accordingly, these balloon catheters are prone to several problems. First, the non-reinforced lumen is susceptible to ovalizing and/or kinking which, in turn, hinders advancement of the catheter over the guidewire, as well as deflation of the balloon. Second, the single lumen is in communication with the arterial blood flow. As the guidewire and balloon catheter are manipulated through the circulatory system, blood is withdrawn into the single lumen of the balloon catheter. Blood may thereby enter the balloon during inflation and cause (1) poor imaging of the balloon, for example, poor fluoroscopic imaging; (2) poor passage of the balloon through the circulatory system due to the premature inflation of the balloon; and (3) poor deflation of the balloon due to blood coagulation in the balloon inflation/deflation port. An additional disadvantage of single lumen balloon catheters is that the interference fit of the guidewire and inflation seal of the balloon may result in removal or peeling of the hydrophilic coating of the guidewire.

In order to minimize the outer diameter, current balloon catheters intended for neurological procedures are also typically designed to work with only a narrow gauge guidewire that is supplied by a manufacturer along with the balloon catheter. The current balloon catheters employ guidewires having diameters in the range of 0.010 to 0.012 inches. These relatively narrow guidewires are soft and, therefore, are very difficult to maneuver through the small, tortuous neuroanatomy.

What is needed in the field is a balloon catheter that is operable to use with larger gauge guidewires; resists ovalizing and kinking of the inflation and guidewire lumen(s); and deploys with improved pushability and trackability.

OBJECTS AND SUMMARY OF THE INVENTION

It is the objective of the present invention to provide a balloon catheter that is operable to use with large gauge guidewires; that resists ovalizing and kinking of the inflation and guidewire lumen(s); and that deploys with improved pushability and trackability.

One embodiment of the present invention achieves these objectives by providing a balloon catheter that employs a reinforced, co-axial, duel lumen design. In certain embodiments, the lumen are formed of a multilayer, tubular element in which one of the layers functions, in part, to provide radial reinforcement to the tubular element.

In another embodiment of the present invention the distal portion of an outer lumen is locked or fixed to a portion of an inner lumen. A proximal portion of a balloon is attached to a distal portion of the outer lumen and a distal portion of the balloon is attached to a distal portion of the inner lumen. In another embodiment a fluid flow passage is provided between the outer lumen and an interior volume of the balloon, and a passage exclusive to gas or air is formed from the interior volume of the balloon longitudinally through a distal portion of the balloon catheter.

In certain other embodiments de-airing channels or features are employed between an exterior surface of the inner lumen and an interior surface of the balloon in order to facilitate purging of gas from the inflation passageway of the balloon catheter.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 2 is a partial elevation view of a balloon catheter according to one embodiment of the present invention.

FIG. 3 is a cross-sectional view taken along line A-A of FIG. 1 of a balloon catheter according to one embodiment of the present invention.

FIG. 4A is a partial elevation view of an outer assembly of a balloon catheter according to one embodiment of the present invention.

FIG. 4B is a cross-sectional view taken along line C-C of FIG. 4A of an outer assembly of a balloon catheter according to one embodiment of the present invention.

FIG. 5A is a partial elevation view of an inner assembly of a balloon catheter according to one embodiment of the present invention.

FIG. 5B is a cross-sectional view taken along line D-D of FIG. 5A of an inner assembly of a balloon catheter according to one embodiment of the present invention.

DESCRIPTION OF EMBODIMENTS

Figure 1:
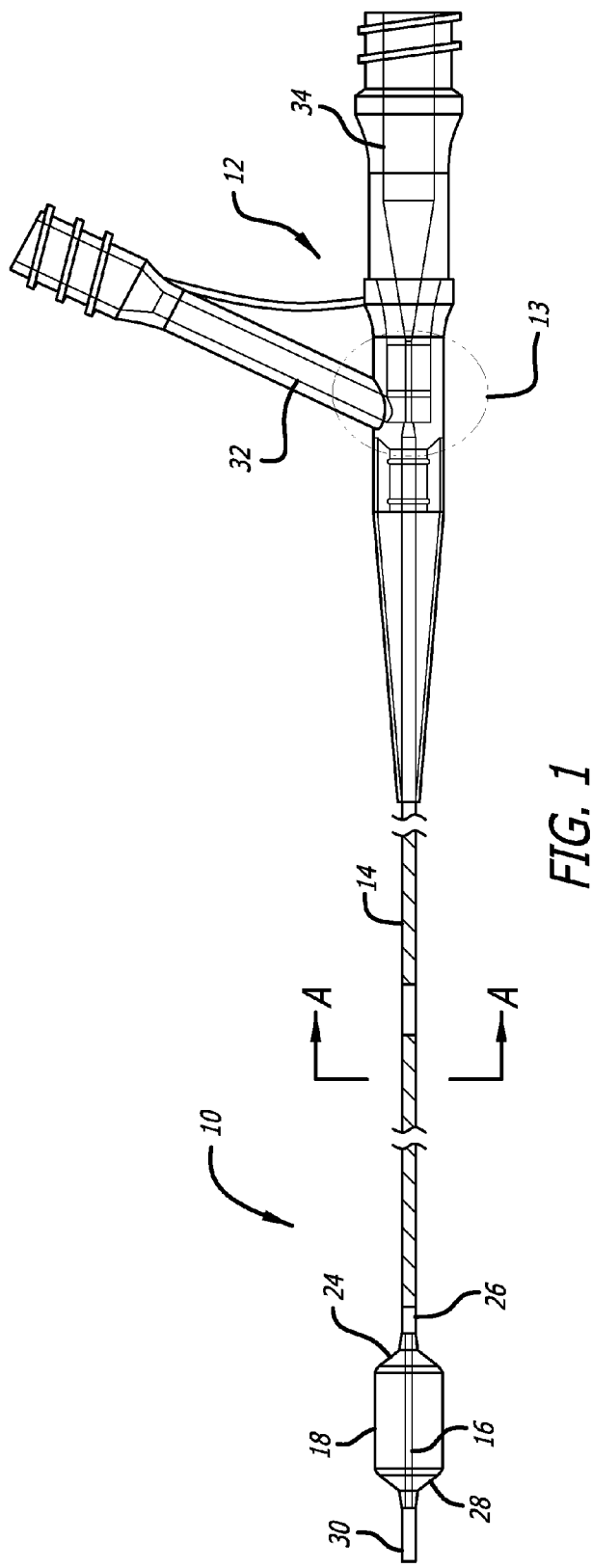
FIG. 1 is an elevation view of a balloon catheter according to one embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The balloon catheter of the present invention addresses many of the shortcomings of the current balloon catheters intended for use in neurological procedures. Broadly speaking, the balloon catheter of the present invention employs a reinforced, co-axial, duel lumen design. The inner most lumen is operable to serve, among other functions, as a guidewire lumen for over-the-wire type procedures. The outer lumen is operable to serve as an inflation lumen for one or more balloons positioned along the length of the balloon catheter. Each lumen is formed by a multilayer, tubular element in which one of the layers, for example a middle layer in a three-layer embodiment, functions in part to provide radial reinforcement to the tubular element. Accordingly, the balloon catheter of the present invention is operable with larger gauge guidewires; resists ovalizing and kinking of the inflation and guidewire lumens; and deploys with improved pushability and trackability over current balloon catheters intended for use in neurological procedures.

Figure 6:
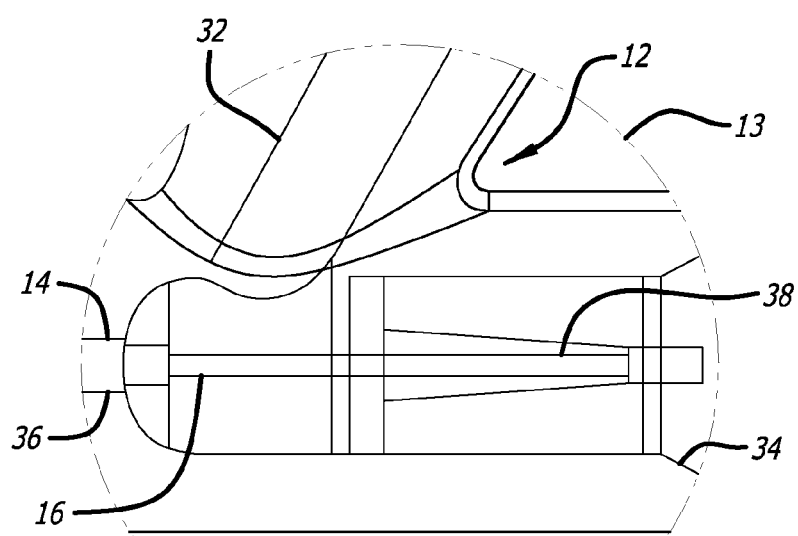
FIG. 6 is an expanded view of region 13 indicated in FIG. 1 of a balloon catheter according to one embodiment of the present invention.

With reference to FIGS. 1-3 and 6, a balloon catheter 10 according to one embodiment of the present invention comprises a hub 12, a balloon 18, and an outer assembly 14 having a lumen 20 through which an inner assembly 16 is co-axially positioned. As best shown in FIG. 6, an expanded view of region 13 indicated in FIG. 1, a proximal portion 36 of the outer assembly 14 is associated with an inflation lumen 32 of the hub 12. A proximal portion 38 of the inner assembly 16 extends proximally from the lumen 20 of the outer assembly 14 and is associated with a guidewire port 34 of the hub 12. At an opposite end of the catheter, a proximal portion 24 of the balloon 18 is associated with a distal portion 26 of the outer assembly 14, and a distal portion 28 of the balloon 18 is associated with a distal portion 30 of the inner assembly 16. Alternatively stated, the opposite ends of the balloon 18 span between the distal portion 26 of the outer assembly 14 and the distal portion 30 of the inner assembly 16.

As shown in FIGS. 4A and 4B, the outer assembly 14 is a tubular structure having a multilayer wall; an inner layer 40, middle layer 42, and outer layer 44. The inner layer 40 of the outer assembly 14 is formed of a longitudinally continuous or segmented tubular element. In embodiments in which the inner layer 40 of the outer assembly 14 is formed of longitudinally segmented tubular elements the individual segments may be fabricated from the same or different materials and may be attached to one another by welding, fusing, adhering, melting, or other polymerizing or non-polymerizing methods. The inner layer 40 of the outer assembly 14 is fabricated from one or more different polymeric materials, or, alternatively, the inner layer 40 of the outer assembly 14 is formed of a single etched polytetrafluoroethylene, PTFE, tube. While a variety of materials are contemplated for use in fabricating the inner layer 40 of the outer assembly 14, of particular importance is the feature that the material from which the inner layer 40 is formed has a higher melting temperature than the temperature employed to fuse or otherwise attach the outer layer 44 to the inner layer 40 and middle layer 42 of the outer assembly 14.

In one embodiment of the present invention, the middle layer 42 of the outer assembly 14 comprises a wire 46 wound in a coil-like form around the outer surface 48 of the inner layer 40 of the outer assembly 14. The wire 46 may be wound in a single layer from one end of the inner layer 40 to the other end to form a coil-like structure or, alternatively, may be wound repeatedly from one end of the inner layer 40 to the other end to form a multilayer coil-like form, as shown in FIG. 4A. In embodiments employing the middle layer 42 having a multilayered coil-like form, the different windings may be formed from a single or multiple independent wires 46. The wire 46 may have a circular, rectangular, triangular, or flattened ribbon-like cross-sectional shape, or combinations thereof. The wire 46 is fabricated from a variety of polymeric and/or metallic materials, for example stainless steel. The wire 72 has a diameter that is variable or consistent along the length of the wire 72. For example, the wire 72 may have a diameter of approximately 0.001 inches. It is also contemplated that the middle layer 42 be formed of a mesh, a braid, and/or an interweaving of one of more wires 46.

The pitch of the winding of the wire 46 may be either consistent or varied along the length of the inner layer 40. For example, a first proximal segment of the winding may have a pitch of approximately 0.003 inches, a second more distal segment may have a pitch of approximately 0.0035 inches, a third more distal segment may have a pitch of approximately 0.004 inches, a fourth more distal segment may have a pitch of approximately 0.0045 inches, a fifth more distal segment may have a pitch of approximately 0.005 inches, and a sixth more distal segment may have a pitch of approximately 0.001 inches. In embodiments employing the middle layer 42 having a multilayered coil-like form the outer most winding may, for example, have a pitch of approximately 0.100 inches.

In one embodiment of the present invention, the outer layer 44 of the outer assembly 14 comprises a longitudinally continuous or segmented tubular element. The outer layer 44 of the outer assembly 14 is formed of longitudinally segmented, non-heat shrinkable, tubular elements. The individual segments may be fabricated from the same or different materials and may be attached to one another by welding, fusing, adhering, melting, or other polymerizing or non-polymerizing methods, or combinations thereof.

In one embodiment, the outer layer 44 of the outer assembly 14 is fabricated from multiple different polymeric tubular segments. For example, a proximal segment 50 of the outer layer 44 of the outer assembly 14 may be formed of a tubular polyamide such as Girlamid L25. The proximal segment 50 has a length 51, of, for example, approximately 110 centimeters. A second more distal segment 52 may be formed of a tubular poly ether block amide such as Pebax 72D. The second more distal segment 52 has a length 53, of, for example, approximately 10 centimeters. A third more distal segment 54 may be formed of a tubular poly ether block amide such as Pebax 63D. The third more distal segment 54 has a length 55, of, for example, approximately 5 centimeters. A forth more distal segment 56 may be formed of a tubular poly ether block amide such as Pebax 55D. The forth more distal segment 56 has a length 57, of, for example, approximately 20 centimeters. A fifth more distal segment 58 may be formed of a tubular poly ether block amide such as Pebax 45D. The fifth more distal segment 58 has a length 59, of, for example, approximately 10 millimeters. A sixth more distal segment 60 may be formed of a polyolefin such a Plexar. The sixth more distal segment 60 has a length 61, of, for example, approximately 2 millimeters. A distal most segment 62 may be formed of a polyolefin such an Engage 8003. The distal most segment 62 has a length 63 of, for example, approximately 13 centimeters.

The outer assembly 14 may be fabricated by first wrapping the wire 46 around the inner layer 40 thereby forming the middle layer 44. The tubular segment or segments of the outer layer 44 are then slid over the middle layer 42. A heat shrinkable tube of, for example, fluorinated ethylene propylene, FEP, is then slid over the outer layer 44. The FEP is heated so as to deliver heat to the outer layer 44, and the outer layer 44 then softens to encapsulate the wire 46. The FEP tube is then removed from the outer layer 44.

In one embodiment of the present invention, the outer diameter of the outer layer 44 of the outer assembly 14 is in the range of 0.03 to 0.040 inches. The lumen 20 of the outer assembly 14 may have a diameter between 0.020 to 0.029 inches. In one embodiment, the lumen 20 of the outer assembly 14 may have a diameter of approximately 0.0285 inches.

As shown in FIGS. 5A and 5B, the inner assembly 16 is a tubular structure having a multilayer wall formed of an inner layer 64, middle layer 66, and outer layer 68. The inner layer 64 of the inner assembly 16 is formed of a longitudinally continuous or segmented tubular elements. In embodiments in which the inner layer 64 of the inner assembly 16 is formed of longitudinally segmented tubular elements, the individual segments may be fabricated from the same or different materials and may be attached to one another by welding, fusing, adhering, melting, or other polymerizing or non-polymerizing methods, or combinations thereof. The inner layer 64 of the inner assembly 16 is fabricated from one or more different polymeric materials, or, alternatively, the inner layer 64 of the outer assembly 14 is formed of a single, non-segmented, etched polytetrafluoroethylene, PTFE, tube. While a variety of materials are contemplated for use in fabricating the inner layer 64 of the inner assembly 16, it is important to employ a material that has a higher melting temperature than the temperature employed to fuse or otherwise attach the outer layer 68 to the inner layer 64 and middle layer 66 of the inner assembly 16. It is also desirable to employ a material that has a relatively low co-efficient of friction.

In one embodiment of the present invention, the middle layer 66 of the inner assembly 16 comprises a wire 70 wound in a coil-like form around the outer surface 72 of the inner layer 64 of the inner assembly 16. The wire 72 may be wound in a single layer from one end of the inner layer 64 to the other or, alternatively, may be wound repeatedly from one end of the inner layer 64 to the other to form a multilayer coil-like form, as shown in FIG. 4A regarding wire 46 of the outer assembly 14. In embodiments employing the middle layer 66 having a multilayered coil-like form, the different coils may be formed from a single or multiple independent wires 72. The wire 72 may have a circular, rectangular, triangular, flattened, ribbon-like cross-sectional shape, or a combination thereof. The wire 72 may be fabricated from a variety of metallic and/or polymeric materials, for example stainless steel. The wire 72 may have a diameter that is variable or consistent along the length of the wire 72. For example, the wire 72 may have a diameter of approximately 0.001 inches. It is also contemplated that the middle layer 42 may be formed of a mesh or interweaving of one of more wires 46.

The pitch of the winding of the wire 72 may be either consistent or varied along the length of the inner layer 64 of the inner assembly 16. For example, a first proximal segment of the wire 72 winding may have a pitch of approximately 0.003 inches, a second more distal segment may have a pitch of approximately 0.003 inches, and a third most distal segment may have a pitch of approximately 0.001 inches.

As shown in FIGS. 2 and 5A, in one embodiment of the present invention, one or more marker bands 82A, 82B, and 82C are placed, for example, over the wire 70 forming the middle layer 66 of the inner assembly 16. The marker bands 82A, 82B, and 82C comprise a radiopaque material such as gold, platinum, or silver, and are used for determining the location of the balloon catheter 10 within a patient. In certain embodiments of the present invention the maker band 82A may be placed a distance L3 proximate to a distal end 86 of the inner assembly 16. For example, the distance L3 may be 5 millimeters.

The marker bands 82B and 82C may be positioned further proximal of the marker band 82A so as to indicate or mark the proximal portion 24 and the distal portion 28 of the balloon 18. It will be understood that the exact placement of the marker bands 82B and 82C relative to the distal end 86 of the inner assembly 16 will depend on the dimensions of the balloon 18 employed in the balloon catheter 10.

For example, in an embodiment employing a balloon 18 of 10 millimeters in length, a proximal end 84 of the marker band 82C is a distance L1 from the distal end 86 of the inner assembly 16. For example, the distance L1 may be approximately 19.5 millimeters. Opposite ends of the marker bands 82B and 82C are a distance L2 from one another. For example, the distance L2 may be 10 millimeters. In an embodiment employing a balloon 18 of 20 millimeters in length, the distance L1 is, for example, approximately 29.5 millimeters, and the distance L2 is, for example, 20 millimeters. In another embodiment, the marker band 82C may be placed directly underneath inflation plug 88.

In one embodiment of the present invention, the outer layer 68 of the inner assembly 16 comprises a longitudinally continuous or segmented tubular element. Preferably the outer layer 68 of the inner assembly 16 is formed of series of longitudinally segmented, non-heat shrinkable, tubular elements. The individual segments are fabricated from the same or different materials and may be attached to one another by welding, fusing, adhering, melting, or other polymerizing or non-polymerizing methods. Preferably, the outer layer 68 of the inner assembly 16 is fabricated from multiple different polymeric tubular segments. For example, a proximal segment 74 of the outer layer 68 of the inner assembly 16 may be formed of a tubular poly ether block amide such as Pebax 63D. The proximal segment 74 has a length 75 of, for example, approximately 150 centimeters. A second more distal segment 76 may be formed of a tubular poly ether block amide such as Pebax 45D. The second more distal segment 76 has a length 77 of, for example, approximately 10 centimeters. A third more distal segment 78 may be formed of a polyolefin such as Plexar 3080. The third more distal segment 78 has a length 79 of, for example, approximately 2 millimeters. A distal most segment 80 may be formed of a polyolefin such as Engage 8003, and have a length 81 of, for example, approximately 5 centimeters.

The inner assembly 16 may be fabricated by first wrapping the wire 70 around the inner layer 64 thereby forming the middle layer 66. Next, the marker bands 82A, 82B, and 82C are placed over or within the middle layer 66, and the tubular segment or segments of the outer layer 68 are then slid over the marker bands 82A, 82B, and 82C and the middle layer 66. A heat shrinkable tube of, for example, fluorinated ethylene propylene, FEP, is then slid over the outer layer 68. The FEP is heated so as to deliver heat to the outer layer 68, thereby softening the outer layer 68 so as to encapsulate the wire 70 forming the middle layer 66. The FEP tube is then removed from the outer layer 68.

In one embodiment of the present invention, the wire 70 forming the middle layer 66 of the inner assembly 16 may terminate proximal of the distal end 86 of the outer assembly 16. A tubular element 100 may be employed in all or a portion of the length between the distal end 86 and the point at which the wire 70 terminates. The tubular element 100 may, for example, be formed of a crosslinked polyolefin tube having a length of approximately 5 millimeters.

In one embodiment of the present invention, the outer diameter of the outer layer 68 of the inner assembly 16 is in the range of 0.015 to 0.025 inches, and more preferably in the range of 0.020 to 0.0225 inches.

Figure 5C:
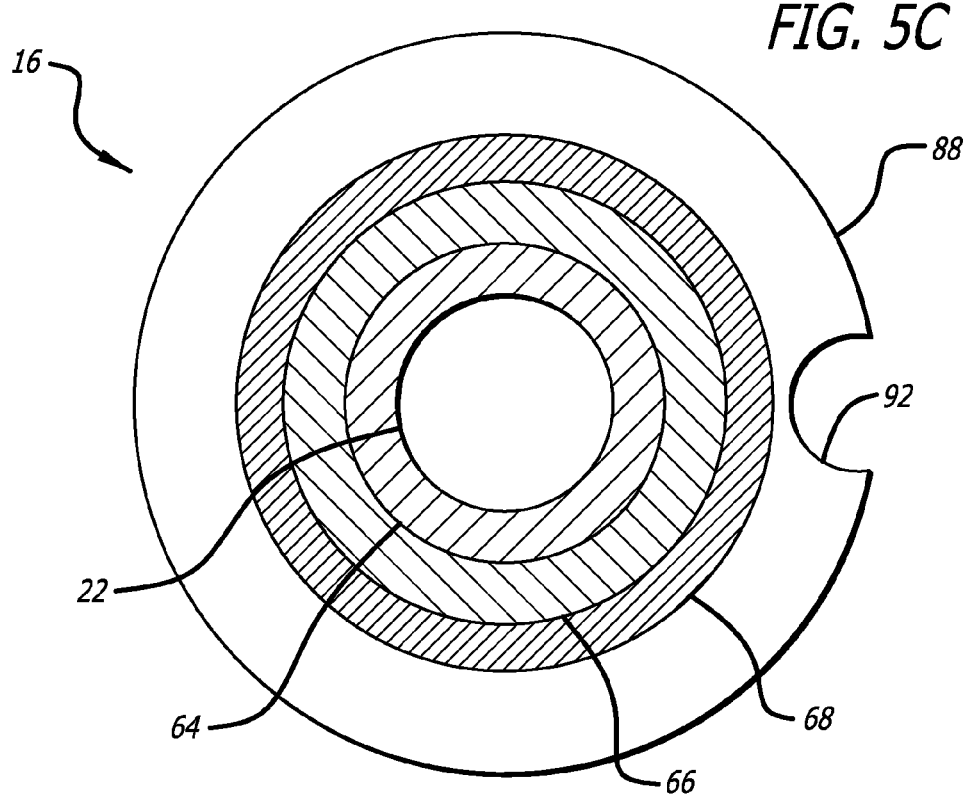
FIG. 5C is a cross-sectional view taken along line E-E of FIG. 5A of an inner assembly of a balloon catheter according to one embodiment of the present invention.

As shown in FIGS. 2, 5A, and 5C, in one embodiment of the present invention, the inner assembly 16 may further comprise an inflation plug 88. The inflation plug 88 is formed of a tubular segment of material having a wall of either uniform or asymmetric thickness. In some embodiments, the inflation plug may have a durometer ranging between 18A to 55D. The inflation plug 88 may, for example be formed of a poly ether block amide such as Pebax 55D. The inflation plug may, for example, be approximately 5 millimeters in length and a distal end 90 of the inflation plug 88 may, for example, be positioned approximately 4 millimeters from the proximal end 84 of the marker band 82C. An outer dimension or diameter of the inflation plug 88 is large enough so that the inflation plug 88 may not completely pass into the lumen 20 of the outer assembly without significant force. The inflation plug 88 may be formed on the inner assembly 16 as described above regarding the formation of the outer layer 68 of the inner assembly 16.

As shown in FIG. 5C, the inflation plug 88 may comprise one or more passages or channels 92 formed longitudinally along the length of the inflation plug. The channel 92 may be formed by placing a mandrel longitudinally along the outside surface of the inflation plug 88 prior to sliding the heat shrinkable tube of, for example, FEP over the inflation plug 88. When the FEP is heated so as to deliver heat to the inflation plug 88, the mandrel melts into the inflation tube thereby the channel 92 within the inflation plug 88. The FEP tube is then removed from the inflation plug 88.

The inflation plug 88 functions, in part, to longitudinally lock the inner assembly 16 to the outer assembly 14 so as to prevent changes in the length of the distal extension of the distal portion 30 of the inner assembly 16 relative to a distal end 98 of the outer assembly 14 due to the inflation and orientation of the balloon 18 during a procedure. The passage or channel 92 formed in the plug 88 allows for fluid communication between the lumen 20 of the outer assembly and an interior volume of the balloon 18.

A shown in FIGS. 3, 5B, 5C, and 7, the inner assembly 16 comprises an inner lumen 22. The lumens functions as a guidewire lumen for over-the-wire procedures. The lumen 22 of the inner assembly 16 may have a diameter of at least approximately 0.0165 inches. Accordingly, the balloon catheter 10 of the present invention may be used with guidewires having a larger diameter than the guidewires supplied with current balloon catheters intended for use in neurological procedures. For example the present balloon catheter 10 may be used with a guidewire having a diameter of 0.014 inches. This feature allows a physician to more easily access a neuroanatomical target, such as an aneurysm, since the relatively larger guidewire provides more support for the balloon catheter 10 over which to track.

Additionally, the guidewire may be removed from the lumen 22 after placement of the balloon catheter within a patient and the lumen 22 may serve as a functional lumen for passage of additional medical devices or substances to the target location within the patient.

It will be understood that it is generally beneficial for the outer assembly 14 and the inner assembly 16 to be more flexible at their distal portions than their proximal portions. Furthermore, it is contemplated that the distal portions of the outer assembly 14 and/or the inner assembly 16 may be pre-shaped or operable to be shaped by a physician prior to initiating a procedure using, for example, steam shaping techniques.

As shown in FIGS. 1 and 6, the proximal portion 36 of the outer assembly 14 terminates distally of the proximal portion 38 of the inner assembly 16. Accordingly, the lumen 20 of the outer assembly is in communication with the inflation port 32. FIGS. 1 and 6 also show that the proximal portion 38 of the inner assembly 16 extends proximally beyond the proximal portion 36 of the outer assembly 14 and is associated with the guidewire port 34 of the hub 12. Accordingly, the lumen 22 of the inner assembly and the guidewire port 34 of the hub 12 together form a substantially continuous lumen through which a guidewire or other medical device may pass. The outer assembly 14 and the inner assembly 16 may be attached to the hub 12 by various methods, including welding, fusing, adhering, melting, or other polymerizing or non-polymerizing method, or combinations thereof. It is noted that this configuration of the hub 12 and association of the hub 12 with the outer assembly 14 and the inner assembly 16 advantageously provides for the isolation of the lumen 22 of the inner assembly 16 from the lumen 20 of the outer assembly 14. The isolation of these lumens and their functionality serves, in part, to address many of the shortcomings described above regarding the current single lumen balloon catheters intended for neurological procedures.

As shown in FIGS. 1 and 2, the proximal portion 24 of the balloon 18 is associated with the distal portion 26 of the outer assembly 14, and the distal portion 28 of the balloon 18 is associated with the distal portion 30 of the inner assembly 16. The balloon 18 may be attached to the distal portion 26 of the outer assembly 14 and the distal portion 30 of the inner assembly 16 by various methods including welding, fusing, adhering, melting, or other polymerizing or non-polymerizing methods and combinations thereof. In certain embodiments, the distal portion of the balloon 18 covers and extends to the distal end 86 of the inner assembly 16. The balloon 18 may, for example, be formed of Polyblend 45A or other polymeric elastomeric material. The balloon 18 may have an outer diameter of up to approximately 15 millimeters and a length in the range of 5 to 50 millimeters and, preferably a length in the range of 10 to 20 millimeters.

Figure 7:
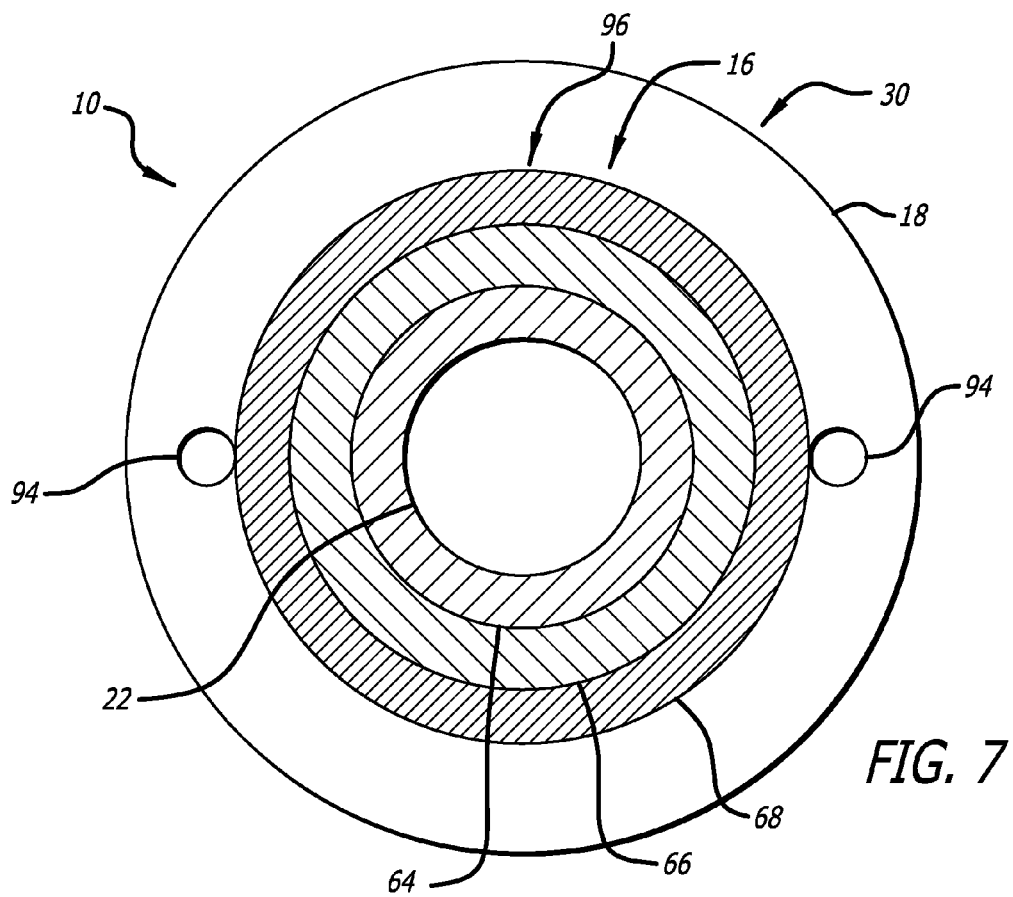
FIG. 7 is a cross-sectional view taken along line B-B of FIG. 2 of an inner assembly of a balloon catheter according to one embodiment of the present invention.

As shown in FIG. 7, in one embodiment of the present invention, one or more air purge ports 94 are employed at the interface of the distal portion 30 of the inner assembly 16 and the distal portion 28 of the balloon 18. The air purge ports 94 are formed by placing one of more mandrels having diameters in the range of 0.0005 to 0.030 inches on the outer surface of the outer layer 68 of the inner assembly 16. An interior surface 96 of the balloon 18 is then attached over the mandrels to the outer layer 68 of the inner assembly 16.

After the balloon 18 is attached to the distal portion 30 of the inner assembly 16 the mandrels are removed. Accordingly, flow paths large enough for the passage of gas and small enough to seal against the passage of liquids are formed.

The air purge ports 94 function to facilitate removal of air from the lumen 20 and balloon 18 prior to initiating a medical procedure. With current co-axial balloon catheters, it is very difficult to remove all of the air from the inflation/deflation lumen prior to initiating a medical procedure. Physicians typically must remove the air from a balloon catheter through several minutes of aspiration or suction through the inflation/deflation lumen. Air that is not removed will show in images taken during the procedure and may obscure details that the physician may otherwise need to observe in order to perform the procedure.

In contrast, the air purge ports 94 of the present invention allow a user to more effectively and more efficiently remove air from the lumen 20, the inflation/deflation lumen. In practice, prior to initiating the procedure, a physician would position the distal end of the balloon catheter 10 higher than the proximal end and then inject a balloon inflation medium, such as contrast medium or saline, through the inflation port 32 and associated lumen 20. As the inflation medium fills the lumen 20, air is forced out the air purge ports 94 until no air remains within the lumen 20 or balloon 18. The physician may repeat the process as needed to ensure that all air is removed from the lumen 20 of the outer assembly 14 and balloon 18.

Figure 8:
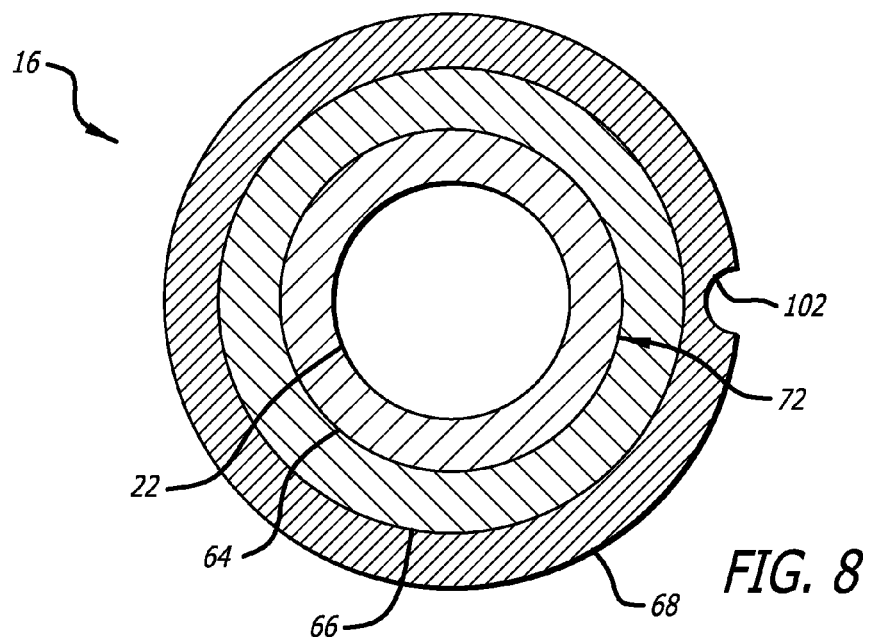
FIG. 8 is a cross-sectional view taken along line D-D of FIG. 5A of an inner assembly of a balloon catheter according to one embodiment of the present invention.
Figure 9:
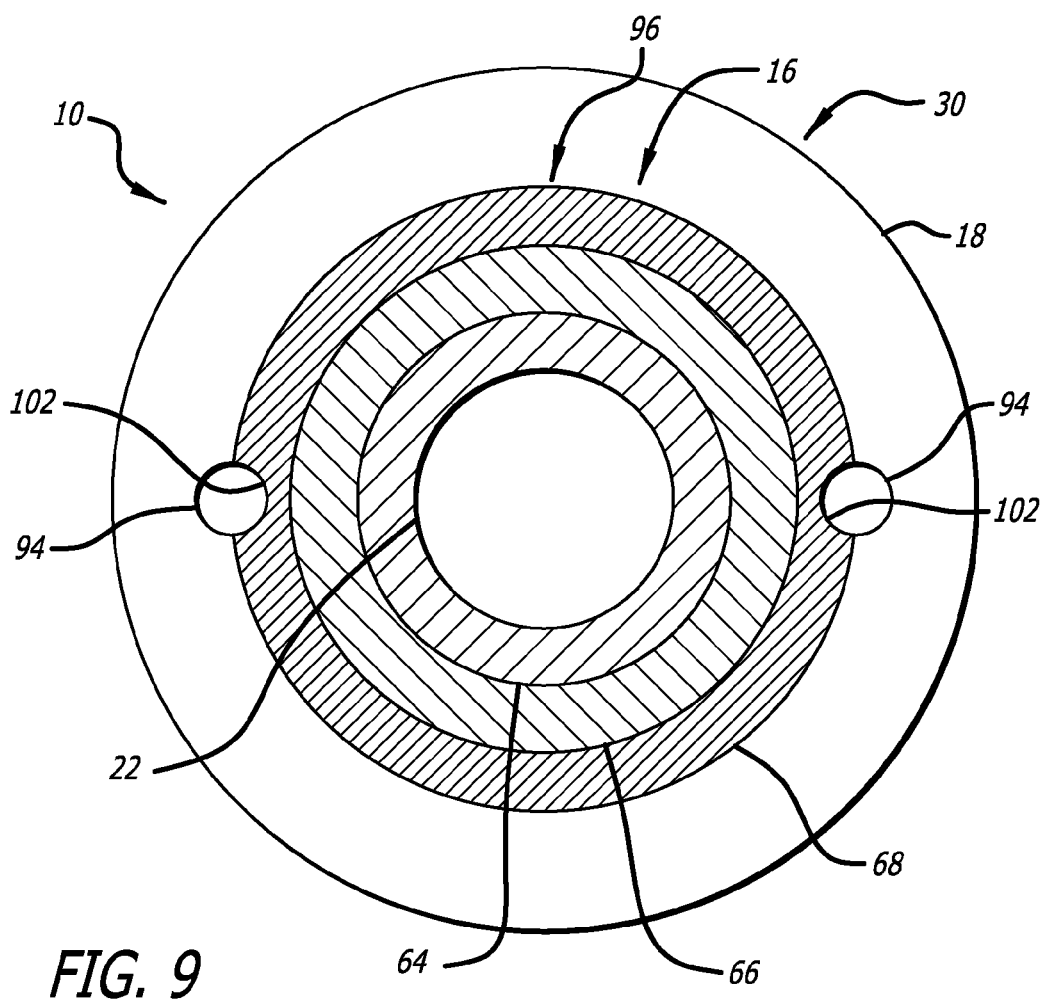
FIG. 9 is a cross-sectional view taken along line B-B of FIG. 2 of an inner assembly of a balloon catheter according to one embodiment of the present invention.

In another embodiment of the present invention, as shown in FIGS. 8 and 9, the above described functionality of the inflation ports 32 is enhanced by employing one or more de-airing channels 102. The de-airing channel 102 is formed in the outer layer 68 of the inner assembly 16. At a minimum, the de-airing channel 102 initiates longitudinally approximate the distal end 90 of the inflation plug 88 and continues uninterruptedly to approximately a proximate end of the air purge port 94. The length of the de-airing channel 102 may extend to or overlap with the distal end 90 of the inflation plug 88 and/or the proximate end of the air purge port 94. The de-airing channel 102 may be either radially aligned or radially off set with the channel 92 of the inflation plug 88 and/or the air purge port 94 relative to an axis through the lumen 22 of the inner assembly 16.

The de-airing channel 102 is formed by placing one of more mandrels having diameters in the range of 0.001 to 0.030 inches between the outer layer 68 of the inner assembly 16 and the heat shrinkable tube and then heating the heat shrinkable tube as described above. In certain embodiments, the de-airing channel 102 is radially aligned with the air purge port 94 and/or with the channel 92 formed in the inflation plug 88. For example, FIG. 9 shows an embodiment in which the de-airing channel 102 is radially aligned with the air purge port 94. The de-airing channel 102 and the air purge port 94 each form a portion of a unified channel. In embodiments in which the de-airing channel 102 is radially aligned with the air purge port 94 and/or with the channel 92 formed in the inflation plug 88, the de-airing channel 102 may extend longitudinally the length of the air purge port 94 and/or may extend longitudinally into or proximately beyond the channel 92 formed in the inflation plug 88.

The de-airing channel 102 helps ensure that a fluid and air flow path is maintained unobstructed between the exterior surface of the inner assembly 16 and the interior surface 96 of the balloon 18. Because the balloon 18 may be closely form fitted over the inner assembly 16 when the balloon is not inflated, absent a de-airing channel 102, it may not always be possible to purge air from lumen 20 of the outer assembly 14 without inflating the balloon 18. Hence, the de-airing channel 102 provides a recess or unobstructed channel on the exterior surface of the inner assembly 16 that allows the passage of air and fluid between the deflated balloon and the exterior surface of the inner assembly 16. Hence, air may be purged from the balloon catheter 10 without inflating of the balloon 18.

It is also contemplated that the de-airing channel 102 may take the form of one or more spiral channels or grooves, spiral ridges, and/or longitudinal ridges on the exterior surface of the inner assembly 16. The de-airing channel 102 may also take the form of one or more small tubular elements bonded to the exterior surface of the inner assembly 16.

It is noted that while the present invention has been described with respect to neurological procedures, it is contemplated that certain features of the present balloon catheter also address needs in non-neurological fields.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A balloon catheter comprising:
   a multilayer outer tubular assembly;
   a multilayer inner tubular assembly independent of the outer tubular assembly coaxially inserted within a lumen of the outer tubular assembly;
   a balloon having a proximal end attached directly to a distal portion of the outer tubular assembly and a distal portion attached directly to a distal portion of the inner tubular assembly; and
   one or more de-airing channels formed directly into an exterior surface of an outer layer of the multilayer inner tubular assembly and spanning longitudinally substantially from the distal portion of the outer tubular assembly to one or more air exclusive purge ports formed at a distal end of the balloon catheter longitudinally between an interior surface of the balloon and an exterior surface of the inner tubular assembly.

2. The balloon catheter of claim 1 wherein the outer tubular assembly comprises an inner, middle, and outer layer.

3. The balloon catheter of claim 2 wherein the middle layer of the outer tubular assembly comprises a coil.

4. The balloon catheter of claim 3 wherein the coil is encapsulated.

5. The balloon catheter of claim 3 wherein a pitch of the coil varies along a length of the coil.

6. The balloon catheter of claim 2 wherein the outer layer of the multilayer outer tubular assembly comprises a plurality of different longitudinal sections.

7. The balloon catheter of claim 1 wherein the multilayer inner tubular assembly comprises an inner layer, a middle layer, and the outer layer.

8. The balloon catheter of claim 7 wherein the middle layer of the multilayer inner tubular assembly comprises a coil.

9. The balloon catheter of claim 8 wherein the coil is encapsulated.

10. The balloon catheter of claim 8 wherein a pitch of the coil varies along a length of the coil.

11. The balloon catheter of claim 7 wherein the outer layer of the multilayer inner tubular assembly comprises a plurality of different longitudinal sections.

12. The balloon catheter of claim 1 wherein a lumen of the multilayer inner tubular assembly has a diameter of approximately 0.0165 inches.

13. The balloon catheter of claim 1 wherein an inflation plug is formed on a portion of the inner tubular assembly such that the distal end of the outer tubular assembly is locked to the inner tubular assembly so as to substantially prevent a change in an entire length of the balloon due to inflation of the balloon.

14. The balloon catheter of claim 13 wherein the inflation plug comprises a longitudinal passage that allows fluid communication between the lumen of the outer tubular assembly and an interior volume of the balloon.

15. The balloon catheter of claim 13 wherein the one or more de-airing channels span longitudinally from the inflation plug towards a distal end of the balloon.

16. A method for manufacturing a balloon catheter comprising the steps of:
   obtaining a multilayer outer tubular assembly;
   obtaining a multilayer inner tubular assembly distinct from the multilayer outer tubular assembly;
   inserting the multilayer inner tubular assembly through a lumen of the multilayer outer tubular assembly;
   forming an annular void between an inner layer of the multilayer outer tubular assembly and an outer layer of the inner multilayer tubular assembly;
   attaching a proximal end of a balloon to a distal portion of the outer tubular assembly;
   attaching a distal end of the balloon to a distal portion of the inner tubular assembly; and
   forming a longitudinal channel directly into an exterior surface of an outer layer of the multilayer inner tubular assembly that spans longitudinally substantially from the distal portion of the outer tubular assembly to one or more air exclusive purge ports formed at a distal end of the balloon catheter longitudinally between an interior surface of the balloon and the exterior surface of the inner tubular assembly.

17. The method of claim 16 wherein the step of obtaining a multilayer outer tubular assembly comprises obtaining an outer tubular assembly having a reinforcing wire layer interposed between an outer and an inner polymeric, non-wire layer.

18. The method of claim 17 wherein the step of obtaining an outer tubular assembly having a reinforcing wire layer comprises obtaining an outer tubular assembly having a coil.

19. The method of claim 18 wherein the step of obtaining an outer tubular assembly having a coil comprises obtaining an outer tubular assembly having a coil that is encapsulated by the outer polymeric, non-wire layer of the outer tubular assembly.

20. The method of claim 18 wherein the step of obtaining an outer tubular assembly having a coil comprises obtaining an outer tubular assembly having a coil with a variable pitch along a length of the outer tubular assembly.

21. The method of claim 16 wherein the step of obtaining a multilayer inner tubular assembly distinct from the multilayer outer tubular assembly comprises obtaining an inner tubular assembly having a reinforcing wire layer interposed between the outer layer and an inner polymeric, non-wire layer.

22. The method of claim 21 wherein the step of obtaining an inner tubular assembly having a reinforcing wire layer comprises obtaining an inner tubular assembly having a coil.

23. The method of claim 22 wherein the step of obtaining an inner tubular assembly having a coil comprises obtaining an inner tubular assembly having a coil that is encapsulated by the outer polymeric layer of the inner tubular assembly.

24. The method of claim 22 wherein the step of obtaining an inner tubular assembly having a coil comprises obtaining an inner tubular assembly having a coil with a variable pitch along a length of the inner tubular assembly.

* * * * *